US012616408B2

(12) United States Patent
Ishida et al.

(10) Patent No.: US 12,616,408 B2
(45) Date of Patent: May 5, 2026

(54) INTRAVASCULAR DEVICE

(71) Applicant: Epsilon Medical Inc., Tokyo (JP)

(72) Inventors: Hiroki Ishida, Tokyo (JP); Yuji Matsumaru, Tokyo (JP)

(73) Assignee: Epsilon Medical Inc., Tokyo (JP)

(*) Notice: Subject to any disclaimer, the term of this patent is extended or adjusted under 35 U.S.C. 154(b) by 0 days.

(21) Appl. No.: 18/712,879

(22) PCT Filed: Oct. 19, 2023

(86) PCT No.: PCT/JP2023/037796
    § 371 (c)(1),
    (2) Date: May 23, 2024

(87) PCT Pub. No.: WO2024/085206
    PCT Pub. Date: Apr. 25, 2024

(65) Prior Publication Data
    US 2024/0324933 A1      Oct. 3, 2024

(30) Foreign Application Priority Data

Oct. 21, 2022    (JP) ................................. 2022-169232

(51) Int. Cl.
    *A61B 5/05*        (2021.01)
    *A61B 5/00*        (2006.01)
    (Continued)

(52) U.S. Cl.
    CPC ................ *A61B 5/293* (2021.01); *A61B 5/37* (2021.01); *A61B 5/4836* (2013.01);
    (Continued)

(58) Field of Classification Search
    CPC . A61B 2018/00875; A61B 5/318; A61B 8/06; A61B 18/1492; A61B 5/02028;
    (Continued)

(56) References Cited

U.S. PATENT DOCUMENTS 5,184,621 A * 2/1993 Vogel ..................... A61B 5/027
                                                    600/585
5,437,664 A * 8/1995 Cohen ................ A61B 18/1492
                                                    606/49
(Continued)

FOREIGN PATENT DOCUMENTS

CN          113426011 A        9/2021
EP          4282463 A1        11/2023
(Continued)

OTHER PUBLICATIONS

An Office Action mailed by the Chinese Patent Office on Aug. 17, 2024, which corresponds to Chinese Patent Application No. 202380014884.3 and is related to U.S. Appl. No. 18/712,879.
(Continued)

*Primary Examiner* — Joseph A Stoklosa
*Assistant Examiner* — Brian M Antiskay
(74) *Attorney, Agent, or Firm* — Studebaker Brackett PLLC

(57) ABSTRACT

An intravascular device (1) is configured such that a first end section (1*a*) is disposed in a blood vessel of an organism, and an electrode for detection or stimulation of nerve tissue located outside the blood vessel is provided to the first end section (1*a*). The intravascular device (1) includes: an electrically-conductive wire member (10); at least one electrode member (20) that is provided on the first end section (1*a*) side and that is electrically connected to the wire member (10); and difference reduction sections (30, 40) that reduce a level difference caused by an outer diameter difference between the outer diameter of the electrode member (20) and the outer diameter of the wire member (10). The electrical resistance between the electrode member (20) and a second end section (1*b*) of the wire member (10), which is
(Continued)

on the side opposite from the first end section (1a), is 100Ω or less.

11 Claims, 6 Drawing Sheets

(51) Int. Cl.
*A61B 5/293* (2021.01)
*A61B 5/37* (2021.01)
*A61M 25/09* (2006.01)

(52) U.S. Cl.
CPC . *A61B 5/6851* (2013.01); *A61M 2025/09066* (2013.01); *A61M 2025/09191* (2013.01)

(58) Field of Classification Search
CPC .................... A61B 5/021; A61B 5/029; A61B 2018/00107; A61B 5/282; A61B 18/14; A61B 5/283; A61N 1/05; A61N 1/0551; A61N 1/056; A61N 1/0472; A61M 25/0009
USPC ................ 600/372–374, 377–378, 381, 393, 600/433–435, 508–509, 544–545; 606/32, 48; 607/115–119
See application file for complete search history.

(56) References Cited

U.S. PATENT DOCUMENTS

| | | | | |
|---|---|---|---|---|
| 5,549,109 | A | 8/1996 | Samson et al. | |
| 5,645,064 | A * | 7/1997 | Littmann | A61B 5/287 600/374 |
| 5,645,082 | A | 7/1997 | Sung et al. | |
| 5,706,809 | A | 1/1998 | Littmann et al. | |
| 6,251,107 | B1 * | 6/2001 | Schaer | A61B 18/1492 606/41 |
| 6,254,550 | B1 * | 7/2001 | McNamara | A61M 25/09 600/585 |
| 8,348,137 | B1 * | 1/2013 | Perera | B23K 3/0638 228/259 |
| 2002/0147487 | A1 * | 10/2002 | Sundquist | A61N 1/056 607/122 |
| 2003/0143895 | A1 * | 7/2003 | Sommer | A61N 1/3752 439/668 |
| 2009/0306651 | A1 * | 12/2009 | Schneider | A61B 5/287 606/41 |
| 2012/0130220 | A1 | 5/2012 | Maskara et al. | |
| 2016/0113710 | A1 * | 4/2016 | Ogle | A61M 25/0012 606/41 |
| 2020/0268442 | A1 * | 8/2020 | Paamand | A61B 18/1492 |
| 2024/0099631 | A1 | 3/2024 | Matsumaru | |

FOREIGN PATENT DOCUMENTS

| | | | | |
|---|---|---|---|---|
| JP | H08-506034 | A | 7/1996 | |
| JP | 2007-111118 | A | 5/2007 | |
| JP | 2013-536743 | A | 9/2013 | |
| JP | 2022-121975 | A | 8/2022 | |
| WO | 2012/067935 | A1 | 5/2012 | |
| WO | WO-2022079672 | A1 * | 4/2022 | A61B 18/1482 |
| WO | 2022/172694 | A1 | 8/2022 | |

OTHER PUBLICATIONS

International Search Report issued in PCT/JP2023/037796; mailed Jan. 9, 2024.

Written Opinion of the International Searching Authority issued in PCT/JP2023/037796; mailed Jan. 9, 2024.

The extended European search report issued by the European Patent Office on Jan. 31, 2025, which corresponds to European Patent Application No. 23879849.0-1113 and is related to U.S. Appl. No. 18/712,879.

Communication pursuant to Article 94(3) EPC issued by the European Patent Office on Feb. 3, 2026, which corresponds to European Patent Application No. 23879849.0-1113 and is related to U.S. Appl. No. 18/712,879.

* cited by examiner

INTRAVASCULAR DEVICE

TECHNICAL FIELD

The present disclosure relates to an intravascular device configured to be used to detect or stimulate activity in nerve tissue.

BACKGROUND ART

In the related art, in a case in which brain waves of a living organism such as an animal or a human being are measured, electrodes are attached to a scalp of the living organism to perform transcranial measurements that measure the brain waves. According to this method, brain waves can be easily measured, but the method has the following drawbacks. Only information from a surface of a brain can be obtained, and thus only brain waves in a vicinity of the surface of the brain can be measured, and brain waves that are generated in a deep portion of the brain cannot be measured. Further, brain waves attenuate upon passing through the skull, thus accurate measurement is difficult.

As a means for overcoming such disadvantages, Patent Document 1 discloses a device that is used to detect or stimulate activity in nerve tissue.

CITATION LIST

Patent Document

Patent Document 1: Japanese Unexamined Patent Application, Publication No. 2022-121975

DISCLOSURE OF THE INVENTION

Problems to be Solved by the Invention

However, in the device of Patent Document 1, electrodes are provided exposed from side surfaces of a core material and an insulator, and therefore it is difficult to stably manufacture the electrodes in an ultrafine outer shape so that the electrodes are insertable into, for example, a cerebral blood vessel. Further, in Patent Document 1, the configuration including a helical portion leads to a poor delivery property in a blood vessel.

An object of the present disclosure is to provide an intravascular device that is configured to be used to detect or stimulate activity in nerve tissue, has an excellent delivery property to a blood vessel, and is highly sensitive for detection or stimulation.

Means for Solving the Problems

According to the present disclosure, it is possible to solve the above problems by the following solutions. To facilitate understanding, reference numerals that correspond to the embodiments of the present disclosure are given and described, and the present disclosure is not limited thereto.

A first aspect of the present disclosure relates to an intravascular device (1, 1B, 1C, 1D) having a first end portion (1a) configured to be disposed within a blood vessel of a living organism, and comprising, on a first end portion (1a) side, an electrode that is configured to detect or stimulate activity in nerve tissue that is located outside of the blood vessel, the intravascular device further comprising: a linear delivery member (10) that is electrically conductive; at least one electrode member (20, 21, 22) provided on the first end portion (1a) side and electrically connected to the linear delivery member (10); and a step-reducing portion (30, 40, 70) that is configured to reduce a size of a step due to an outer diameter difference between an outer diameter of the electrode member (20, 21, 22) and an outer diameter of the linear delivery member (10). The intravascular device (1, 1B, 1C, 1D) has an electrical resistance of 100Ω or less between the electrode member (20, 21) and a second end portion (1b) that is opposite to the first end portion (1a) of the linear delivery member (10).

A second aspect of the present disclosure relates to the intravascular device (1, 1C) according to the first aspect, in which the step-reducing portion (30, 40) comprises at least one of a coiled member (30) provided around the linear delivery member (10), a twisted linear member (80) provided around the linear delivery member (10) or along the linear delivery member (10), or a tubular member (40) composed of resin and provided around the linear delivery member (10).

A third aspect of the present disclosure relates to the intravascular device (1, 1C) according to the second aspect, in which at least a portion of the coiled member (30) extends within the electrode member (20, 21).

A fourth aspect of the present disclosure relates to the intravascular device (1, 1C) according to the second aspect or the third aspect, in which at least a portion of the tubular member (40) extends over the coiled member (30).

A fifth aspect of the present disclosure relates to the intravascular device (1D) according to the first aspect, in which the electrode member (22) and the linear delivery member (10) are disposed apart from each other, and the electrode member (22) and the linear delivery member (10) are electrically connected to each other by an electrical conductor (80).

A sixth disclosure of the present disclosure relates to the intravascular device (1D) according to the fifth disclosure, in which the electrical conductor (80) is a coiled wire or a twisted wire.

A seventh disclosure of the present disclosure relates to the intravascular device (1, 1B) according to any one of the first disclosure to the fourth disclosure, in which the electrode member (20) is in a form of a helically wound metal wire.

An eighth disclosure of the present disclosure relates to the intravascular device (1, 1B, 1C) according to any one of the first disclosure to the fifth disclosure, in which the electrode member (20, 21) and the linear delivery member (10) are fused to each other.

A ninth disclosure of the present disclosure relates to the intravascular device (1, 1B, 1C) according to any one of the first disclosure to the sixth disclosure, in which the intravascular device (1, 1B, 1C, 1D) is placed in a blood vessel for one day or more.

At tenth disclosure of the present disclosure relates to the intravascular device (1, 1B, 1C) according to any one of the first disclosure to the seventh disclosure, in which the blood vessel, in which the intravascular device (1, 1B, 1C, 1D) is disposed, is a cerebral vein.

Effects of the Invention

According to the present disclosure, it is possible to provide an intravascular device that is configured to be used to detect or stimulate activity in nerve tissue, has an excellent delivery property to a blood vessel, and is highly sensitive for detection or stimulation.

PREFERRED MODE FOR CARRYING OUT THE INVENTION

The following describes a mode of the present disclosure with reference to the accompanying drawings.

First Embodiment

Figure 1:
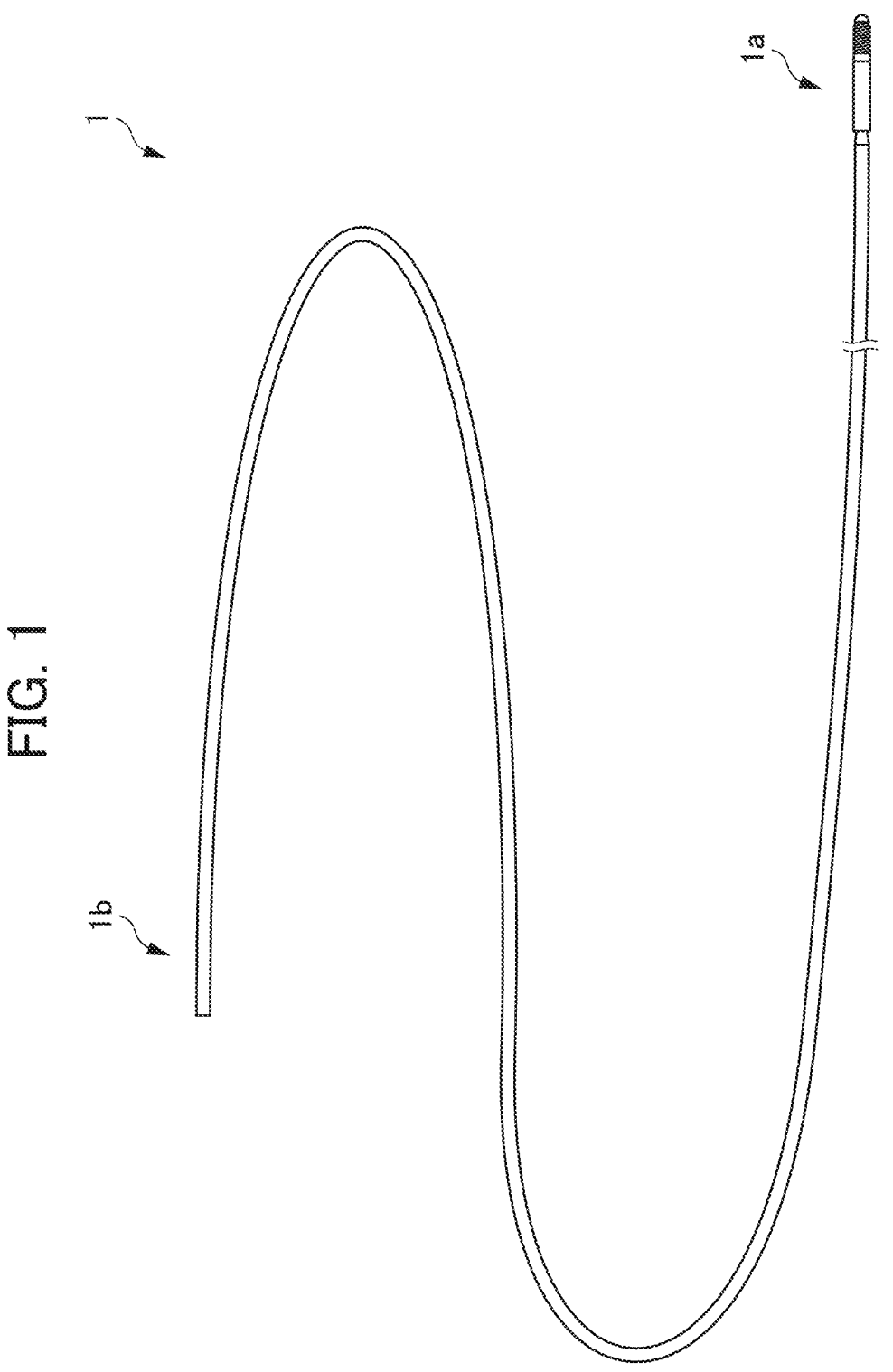
FIG. 1 is a diagram that illustrates a first embodiment of an intravascular device 1 according to the present disclosure.

FIG. 1 is a diagram that illustrates a first embodiment of an intravascular device 1 according to the present disclosure. Each drawing, including FIG. 1, is schematically illustrated, and the size and shape of each portion are exaggerated or omitted as appropriate to ease understanding. Further, in the following description, specific numerical values, shapes, materials, and the like are illustrated and can be appropriately modified.

The intravascular device 1 of a present embodiment is used to detect or stimulate neural activity of a living organism such as an animal or a human being. The intravascular device 1 has flexibility, is formed into an elongated string shape, and has a first end portion 1a and a second end portion 1b. The first end portion 1a is disposed in a blood vessel (typically, a cerebral blood vessel) of the living organism, and the second end portion 1b is electrically connected to a measuring instrument, an oscillator, or the like (not shown). The intravascular device 1 is inserted into the cerebral vein through a catheter that is used in conventional endovascular surgery. At this time, as is described later, the electrode is extremely fine, flexible, attached to a wire member, and has no large irregularity in the outer shape thereof. Therefore, unlike the stent, the electrode has no expansive force, and has excellent sliding ability against the catheter, and thus the electrode has an excellent delivery property to the cerebral blood vessel. Further, contact between the wire member and the blood vessel is reduced or prevented (in particular, in a natural state as in the present embodiment, a string-shaped wire member has almost no contact with a blood vessel wall), and thus an adverse event is less likely to occur even in a case in which the wire member is left in place for a long time. Therefore, it is possible to safely place the wire member in the blood vessel for one day or more (Specifically, 2 days or more, 5 days or more, 7 days or more, 2 weeks or more, or 1 month or more).

Figure 2:
FIG. 2 is an enlarged view of a vicinity of a first end portion 1a of the intravascular device 1.
Figure 2:
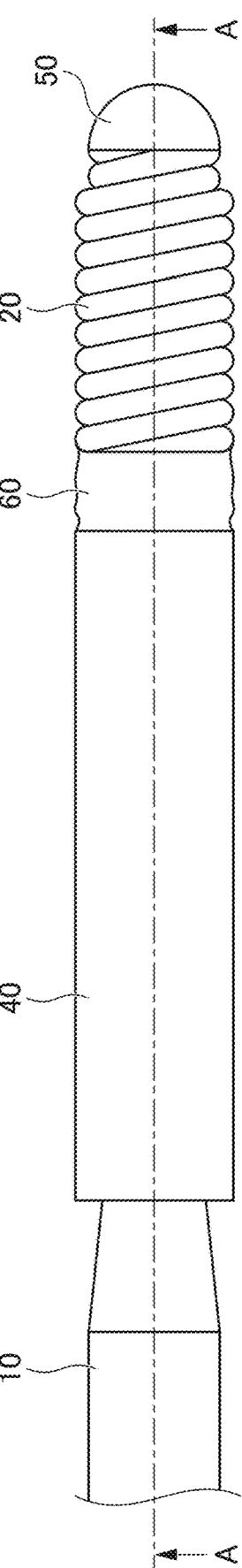
Figure 3:
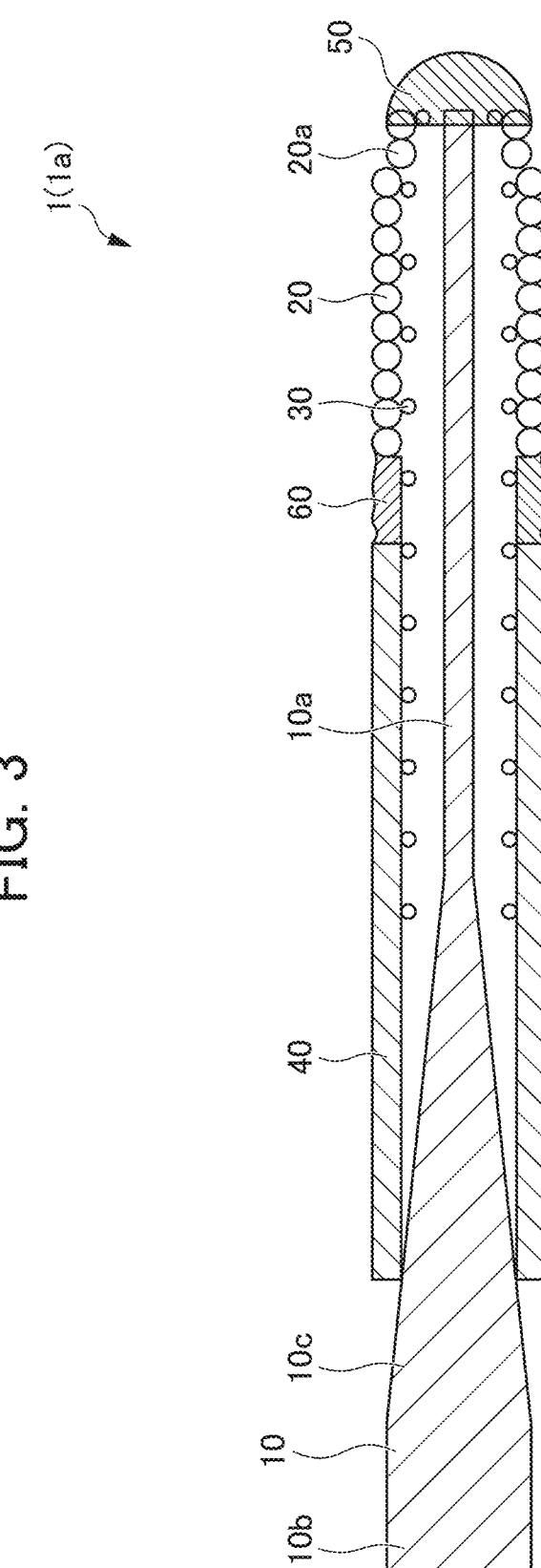
FIG. 3 is a cross-sectional view of the intravascular device 1 taken along a line A-A in FIG. 2.

FIG. 2 is an enlarged view of a vicinity of the first end portion 1a of the intravascular device 1. FIG. 3 is a cross-sectional view of the intravascular device 1 taken along a line A-A in FIG. 2. The intravascular device 1 includes a wire member 10, an electrode member 20, an inner coil 30, a tubular member 40, a tip portion 50, and a connecting portion 60.

The wire member 10 (linear delivery member) is provided extending from the first end portion 1a to the second end portion 1b of the intravascular device 1 and is conductive. The wire member is flexible and is configured in a linear shape (or a string shape or a rod shape) when viewed as a whole and has no inner cavity unlike a tubular body. As the linear delivery member, a straight wire member may be used as in the present embodiment, a twisted wire member may be used, or a member in the form of a coil, a multi-tube coil, or the like may be used. However, it is preferable for the linear delivery member to be a straight wire to reduce the electric resistance between the electrode member 20 and the second end portion 1b. In the present embodiment, a straight wire composed of an alloy of Ni (nickel) and Ti (titanium) is used as the wire member 10. In addition, the wire member 10 is not limited to the above-described material, and for example stainless steel may be used. The wire member 10 has a large diameter portion 10b on a second end portion 1b side, and the large diameter portion 10b can have a diameter of, for example, about 0.25 mm. Further, the wire member 10 has a small diameter portion 10a on a first end portion 1a side, and the small diameter portion 10a is formed to be thinner than the large diameter portion 10b, and can have a diameter of, for example, about 0.05 mm. An outer diameter of the small diameter portion 10a and an outer diameter of the large diameter portion 10b are connected by an outer diameter of a conical surface portion 10c that is gradually tapered. The conical surface portion 10c has an inclination that, in the figures, is exaggerated to emphasize the rate of change. The rate of change of the outer diameter of the conical surface portion 10c may be smaller than that illustrated in the figures. The wire member 10 has an insulating film that is formed on the surface thereof. As the insulating film, for example, PTFE (polytetrafluoroethylene) coating can be used. Further, the wire member 10 may be covered by a tube composed of PTFE, silicon, polyimide, or the like, a heat shrinkable tube, or the like instead of the insulating film. In addition, the insulating film is not provided in a vicinity of a tip (in a vicinity of a first end portion 1a) of the wire member 10. This configuration enables the tip portion 50 that is described later to be welded.

The electrode member 20 is provided around the wire member 10 on the first end portion 1a side and is electrically connected to the wire member 10. The electrode member 20 is configured with an electrical conductor that is provided exposed on the surface of the intravascular device to detect a weak current such as brain waves that are generated in a body of a human or animal and transmit, to the body, a current that is generated by an oscillator. In the present embodiment, the electrode member 20 is in the form of a tightly-wound coil by helically winding a metal wire that is composed of an alloy of Pt (platinum) and W (tungsten). By virtue of using an alloy containing Pt (platinum) for the electrode member 20, visibility when observing with X-rays can be improved. The electrode member 20 has a coiled configuration, and therefore the electrode member 20 also can be flexible, can improve the delivery property to the blood vessel, and can reduce a risk of damage to the blood vessel. The electrode member 20 has a diameter of, for example, 0.1 mm or greater and 0.28 mm or less. In the present embodiment, the diameter of the electrode member 20 is 0.25 mm. In order to appropriately detect and transmit a current, the electrode member 20 has a portion that is exposed to the outside. The portion that is exposed to the outside has a longitudinal length that is preferably 1 mm or greater and more preferably 2 mm or greater. In the present embodiment, the longitudinal length of the electrode member 20 is 3 mm. Further, the electrode member 20 has a tip region 20a. The tip region 20a is an end portion on the first end portion 1a side and may have an outer diameter that is smaller than other portions (portions that are further to the second end portion 1b side than the tip) of the electrode member 20 to improve the delivery property to the blood vessel. In the present embodiment, the tip region 20a of the electrode member 20 is configured to have an outer diameter that is smaller than the other portions of the electrode member 20.

The inner coil 30 is a coiled member provided around the wire member 10. The inner coil 30 has an outer diameter that is slightly smaller than the inner diameter of the electrode member 20. There is a range at the tip (the first end portion 1a side) of the inner coil 30 where the electrode member 20 is provided and the inner coil 30 extends within this range. That is, in this range, the inner coil 30 is disposed between the wire member 10 and the electrode member 20. The range is a longitudinal range (length) by which the inner coil 30 extends within the electrode member 20 and may be a length at which at least a position of the inner coil 30 becomes stable. In the present embodiment, the inner coil 30 extends within the electrode member 20 for the entire range for which the electrode member 20 is provided. In the present embodiment, the longitudinal length (whole length) of the inner coil 30 is 40 mm. The inner coil 30 has a rear end (the second end portion 1b side) that extends within the tubular member 40. In the present embodiment and similarly to the electrode member 20, the inner coil 30 is formed by helically winding a metal wire that is composed of an alloy of Pt (platinum) and W (tungsten). By virtue of using an alloy containing Pt (platinum) for the inner coil 30 similarly to the electrode member 20, it is possible to improve visibility of the inner coil 30 when observing the inner coil 30 with X-rays. Further, by making a material of the inner coil 30 and a material of the electrode member 20 the same, it is possible to improve weldability at the time of welding of the tip portion 50 that is described later. In the present embodiment, an example is given in which the inner coil 30, similarly to the electrode member 20, is composed of an alloy of Pt (platinum) and W (tungsten). The inner coil 30 may be formed from another material such as stainless steel or the like. Further, the inner coil 30 is not in the form of a tightly-wound coil and is in the form of a coils that are spaced apart from each other. With the above configuration, the inner coil 30 also can be flexible, can improve the delivery property to the blood vessel, and can reduce a risk of damage to the blood vessel.

The tubular member 40 is a resin member provided around the wire member 10 and extends over the inner coil 30 for a range in which the inner coil 30 is provided. In the present embodiment, the inner coil 30 is not insulated, and therefore by virtue of pushing the tubular member 40 over and onto the inner coil 30, the inner coil 30 is insulated. In the present embodiment, the longitudinal length (whole length) of the tubular member 40 is 200 mm. The tip (the first end portion 1a side) of the tubular member 40 is disposed close to the rear end (an end portion on the second end portion 1b side) of the electrode member 20. The rear end side (the second end portion 1b side) of the tubular member 40 is positioned in a middle of the conical surface portion 10c of the wire member 10. The tubular member 40 is preferably configured as, for example, a tube composed of a fluororesin such as PTFE, perfluoroalkoxy alkane (PFA) or fluorinated ethylene propylene (FEP), a tube composed of silicon or polyimide, or a heat shrinkable tube. In the present embodiment, a heat shrinkable tube composed of a fluororesin is used as the tubular member 40. The tubular member 40 and the electrode member 20 each have an outer diameter that are substantially the same.

The inner coil 30 and the tubular member 40 have a function as a step-reducing portion that is configured to reduce a size of a step due to an outer diameter difference between the outer diameter of the electrode member 20 and the outer diameter of the wire member 10. That is, by virtue of providing the inner coil 30 such that the inner coil 30 extends over the wire member 10 and extends within the electrode member 20, the size of the step between the outer diameter of the electrode member 20 and the outer diameter of the wire member 10 is reduced. Further, the tubular member 40 extends over the inner coil 30, and therefore there is substantially no step due to the outer diameter difference between the outer diameter of the electrode member 20 and the outer diameter of the wire member 10, and the surface of the electrode member 20 and the surface of the tubular member 40 are substantially flush with each other.

The tip portion 50 is provided at a forwardmost end on the first end portion 1a side and is formed in a substantially hemispherical shape. The tip portion 50 is formed by welding the electrode member 20 and the wire member 10. That is, the tip portion 50 is composed of an alloy obtained by melting and mixing the electrode member 20 and the wire member 10. By virtue of providing the tip portion 50, the electrode member 20 and the wire member 10 are electrically joined to each other. In the present embodiment, the inner coil 30 is welded, in addition to the electrode member 20 and the wire member 10, at the tip portion 50. The inner coil 30 may not necessarily be welded to the tip portion 50.

In order to appropriately detect a current from an extravascular tissue or transmit the current to the extravascular tissue, the electrical resistance between the electrode member 20 and the rear end portion (the end portion on the second end portion 1b side) of the wire member 10 is preferably 100Ω or less, and more preferably 75Ω or less. In the present embodiment, a straight wire is used for the wire member 10, and the electrode member 20 and the wire member 10 are welded to each other at the tip portion 50. Therefore, a very low resistance value of 70Ω or less can be achieved.

The connecting portion 60 connects the rear end portion (the end portion on the second end portion 1b side) of the electrode member 20 and the end portion on the first end portion 1a side of the tubular member 40. The connecting portion 60 may be composed of, for example, an adhesive such as an ultraviolet curing type or a two-component mixture type epoxy adhesive, a cyanoacrylic instant adhesive, or a silicon adhesive.

The intravascular device 1 of the first embodiment described above can be used in various applications. For example, in a case in which the intravascular device 1 of the present embodiment is appropriately disposed in the cerebral blood vessel at a position close to each of the left brain and the right brain to detect brain waves, it is possible to use the intravascular device 1 to identify an epilepsy focus and detect an epilepsy attack. Further, in the case of a disease (epilepsy, depression, involuntary movement due to Parkinson's disease, asthenic-vegetative disorder, or the like) in which a causal site exists in the deep brain portion, by virtue of appropriately disposing the intravascular device of the present disclosure with respect to the causal site and supplying electric stimulation, it is possible to use the intravascular device in the treatment of these diseases.

As described above, according to the intravascular device 1 of the first embodiment, it is possible to facilitate manufacturing due to the intravascular device 1 having a simple configuration that uses the wire member 10, the electrode member 20, the inner coil 30, and the tubular member 40. Further, according to the intravascular device 1 of the first embodiment, it is possible to provide an intravascular device that has an excellent delivery property to a blood vessel, and is highly sensitive for detection or stimulation.

Second Embodiment

Figure 4:
FIG. 4 is a cross-sectional view of an intravascular device 1B of a second embodiment at a position similar to FIG. 3 of the first embodiment.
Figure 4:
Figure 4:
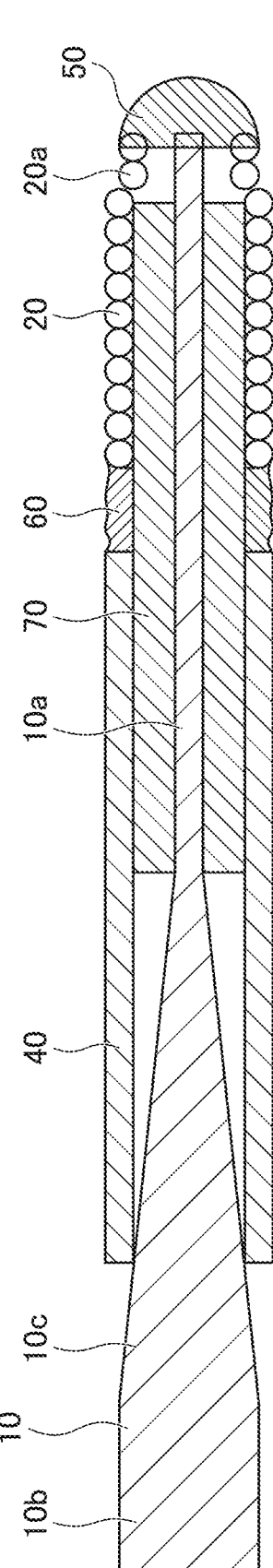

FIG. 4 is a cross-sectional view of an intravascular device 1B of a second embodiment at a position similar to FIG. 3 of the first embodiment. The intravascular device 1B of the second embodiment has the same configuration as the intravascular device 1 of the first embodiment except that a second tubular member 70 is disposed instead of the inner coil 30. Therefore, portions that satisfy the same functions as those of the first embodiment described above are denoted by the same reference numerals, and redundant explanations thereof are appropriately omitted.

The second tubular member 70 has an outer diameter that is slightly smaller than the inner diameter of the electrode member 20. The second tubular member 70 has a tip that extends within the electrode member for a range in which the electrode member 20 is provided at the tip (the first end portion 1a side) of the second tubular member 70. That is, in this range, the second tubular member 70 is disposed between the wire member 10 and the electrode member 20. The second tubular member 70 has a rear end (the second end portion 1b side) that extends within the tubular member 40. The second tubular member 70 is preferably configured as, for example, a tube composed of a fluororesin such as PTFE, perfluoroalkoxy alkane (PFA) or fluorinated ethylene propylene (FEP), a tube composed of silicon or polyimide, or a heat shrinkable tube. In the present embodiment, a tube composed of a fluororesin is used as the second tubular member 70. The second tubular member 70 has an inner diameter that, at least before assembly, is slightly larger than the outer diameter of the small diameter portion 10a of the wire member 10. In a case in which a heat shrinkable tube is used for the second tubular member 70, the inner diameter of the second tubular member 70 after shrinking is equal to the outer diameter of the small diameter portion 10a of the wire member 10.

In the second embodiment described above, the second tubular member 70 is disposed instead of the inner coil 30, and therefore dimensional stability is increased. Pushability has further improved, and therefore the delivery property to the blood vessel can be improved and access to an arbitrary blood vessel can be facilitated.

Third Embodiment

Figure 5:
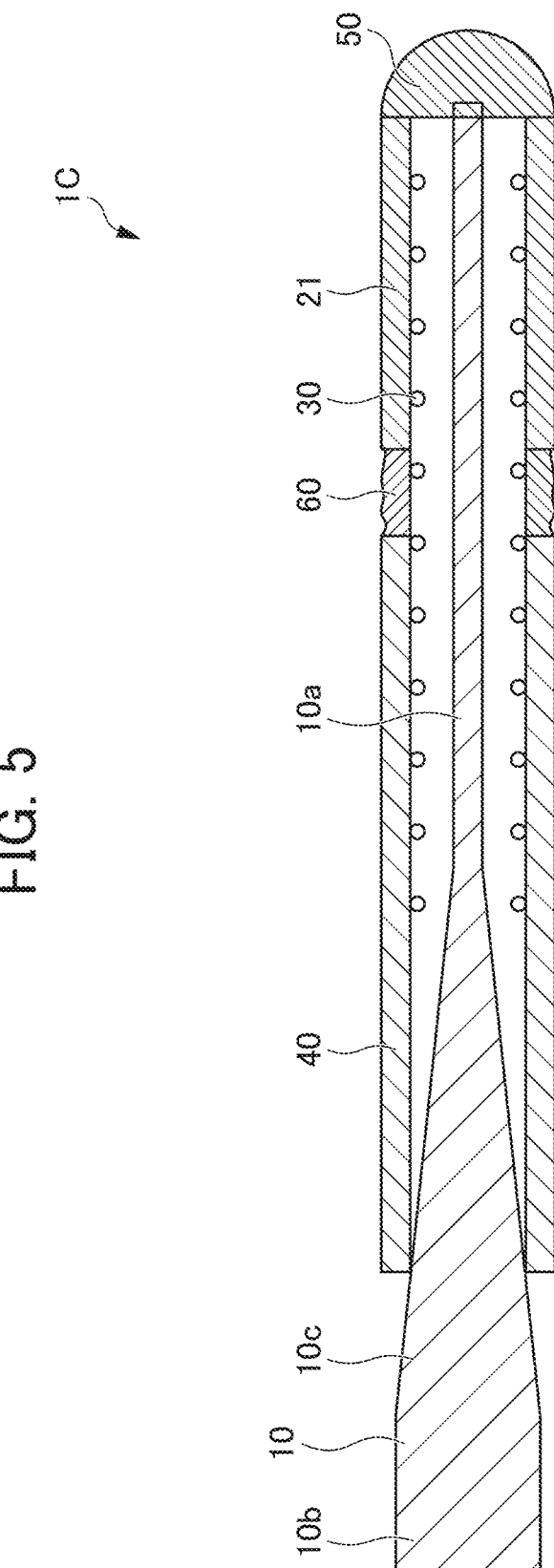
FIG. 5 is a cross-sectional view of an intravascular device 1C of a third embodiment at a position similar to FIG. 3 of the first embodiment.

FIG. 5 is a cross-sectional view of an intravascular device 1C of a third embodiment at a position similar to FIG. 3 of the first embodiment. The intravascular device 1C of the third embodiment has the same configuration as the intravascular device 1 of the first embodiment except that an electrode member 21 is formed differently. Therefore, portions that satisfy the same functions as those of the first embodiment described above are denoted by the same reference numerals, and redundant explanations thereof are appropriately omitted.

The electrode member 21 of the third embodiment is provided at the same position as the electrode member 20 of the first embodiment, but is different from the electrode member 20 of the first embodiment in that the electrode member 21 has a cylindrical shape. The electrode member 21 of the third embodiment can be composed of the same material as the electrode member 20 of the first embodiment.

In the intravascular device 1C of the third embodiment, the electrode member 21 has a cylindrical shape, and therefore it is possible to reduce or prevent corrosion that is likely to occur in a portion where metals are in contact with each other. Therefore, even in a case in which the intravascular device 1C of the third embodiment is placed in a blood vessel over a long period of time, adverse effects such as a decrease in detection capability and signal transmission capability due to corrosion can be prevented.

Fourth Embodiment

Figure 6:
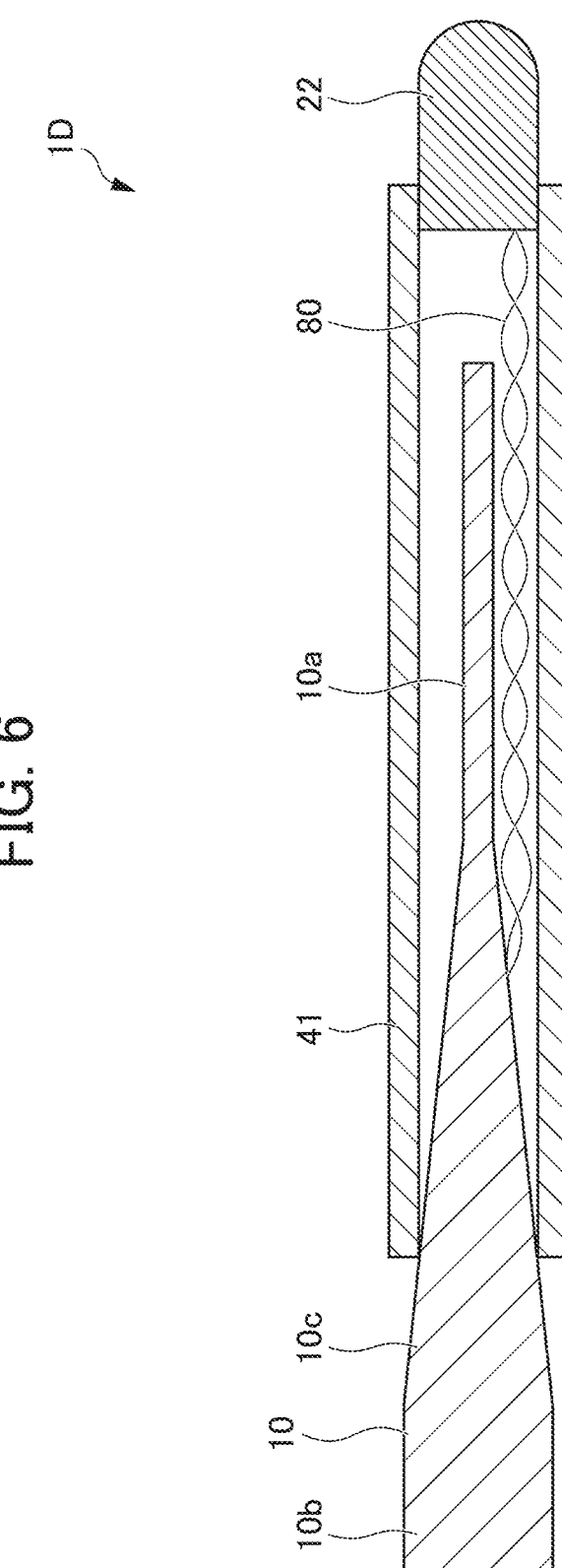
FIG. 6 is a cross-sectional view of an intravascular device 1D of a fourth embodiment at a position similar to FIG. 3 of the first embodiment.

FIG. 6 is a cross-sectional view of an intravascular device 1D of a fourth embodiment at a position similar to FIG. 3 of the first embodiment. The intravascular device 1D of the fourth embodiment has the same configuration as the intravascular device 1 of the first embodiment except that the intravascular device 1D of the fourth embodiment does not include the inner coil 30 of the first embodiment, the electrode member 22 and the wire member 10 are disposed apart from each other, and the intravascular device 1D includes a conductive wire 80. Therefore, portions that satisfy the same functions as those of the first embodiment described above are denoted by the same reference numerals, and redundant explanations thereof are appropriately omitted.

The intravascular device 1D of the fourth embodiment includes a wire member 10, an electrode member 22, a tubular member 41, and an electrically conductive wire 80. The wire member 10 of the fourth embodiment is similar to the wire member 10 of the first embodiment except that the wire member 10 of the fourth embodiment is not in direct contact (welded) with the electrode member 22 and is disposed apart from the electrode member 22.

The electrode member 22 is disposed apart from the wire member 10. The electrode member 22 has a substantially cylindrical shape with a spherical tip. The electrode member 22 may be made of the same material as that of the electrode member 20 of the first embodiment, such as an alloy of Pt (platinum) and W (tungsten).

The tubular member 41 is a resin member provided around the wire member 10, and the tip of the tubular member 41 extends over the electrode member 22 to connect to the electrode member 22. For example, an adhesive may be used to connect the tubular member 41 and the electrode member 22. The tubular member 41 can be formed of the same material as the tubular member 40 of the first embodiment.

The conductive wire 80 is an electrical conductor that electrically connects the wire member 10 and the electrode member 22. In the present embodiment, a twisted wire (twisted linear member) is used that is obtained by twisting a plurality of wire rods made of nickel titanium. The conductive wire 80 is not limited to nickel titanium and may be made of stainless steel, for example. The conductive wire 80 is not limited to a twisted wire and may be a straight wire, and a coil-shaped, rod-shaped, or plate-shaped electrical conductor may be used. FIG. 6 illustrates a configuration in which the conductive wire 80 is connected at the conical surface portion 10*c* of the wire member 10. The conductive wire 80 may be connected at a physical distance that is as short as possible so as to be connected in the vicinity of the tip (in the vicinity of the first end portion 1*a*) of the wire member 10, thereby further reducing the electrical resistance. In the present embodiment, the conductive wire 80 and the tubular member 41 function as a step-reducing portion.

According to the fourth embodiment, the wire member 10 and the electrode member 22 are not fixed to each other, and therefore it is possible to plastically deform the tubular member 41 and reduce a risk of perforation.

Modifications

Various modifications and variations are possible without departing from the scope of the present disclosure, and such modifications and variations are within the scope of the present disclosure.

(1) The first embodiment describes an example in which an inner coil 30 that is helically wound in a coil shape with a regular pitch is disposed as a part of a step-reducing portion. The first embodiment is not limited thereto, and for example, a wire rod having a more linear shape may be disposed along the wire member 10 or wound around the wire member 10 to form a part of the step-reducing portion.

(2) In each embodiment, the electrode member 20 (or the electrode member 21) is disposed at a forwardmost portion of the first end portion 1*a*. Each embodiment is not limited thereto, and for example, the electrode member may be provided at a position away from the forwardmost portion of the first end portion 1*a*, that is, at a position further to the second end portion 1*b* side than the first end portion 1*a*. Further, the number of electrode members is not limited to one, and a plurality of electrode members may be provided.

(3) The first embodiment describes an example in which the inner coil 30 and the tubular member 40 are provided as a step-reducing portion. The first embodiment is not limited thereto, and, for example, the step-reducing portion may be composed of a twisted linear member and a tubular member. In addition to having the form of the conductive wire 80 illustrated in the fourth embodiment, the twisted linear member may be a twisted wire-shaped member formed in a tubular shape by being braided. Further, the twisted linear member may be disposed around the wire member, wound around the wire member, or may be disposed along the wire member.

The embodiments and modifications can be appropriately combined and used, and a detailed description thereof is omitted. Further, the present disclosure is not limited to the embodiments described above.

EXPLANATION OF REFERENCE NUMERALS

1, 1B, 1C intravascular device
1*a* first end portion
1*b* second end portion
10 wire member (linear delivery member)
10*a* small diameter portion
10*b* large diameter portion
10*c* conical surface portion
20 electrode member
20*a* tip region
21 electrode member
30 inner coil (coiled member, step-reducing portion)

40 tubular member (step-reducing portion)
50 tip portion
60 connecting portion
70 second tubular member (step-reducing portion)

The invention claimed is:

1. An intravascular device having a first end portion configured to be disposed within a blood vessel of a living organism, and comprising, on a first end portion side, an electrode that is configured to detect or stimulate activity in nerve tissue located outside of the blood vessel, the intravascular device further comprising:

a linear delivery member that is electrically conductive;

at least one electrode member provided on the first end portion side and electrically connected to the linear delivery member;

a first step-reducing portion that is configured to be at least partially disposed between the electrode member and the linear delivery member to reduce a size of a step due to an outer diameter difference between an outer diameter of the electrode member and an outer diameter of the linear delivery member; and a second step-reducing portion arranged on an outer side of the first step-reducing portion and adjacent to the first step-reducing portion, wherein an outer surface of the second step-reducing portion and the outer surface of the electrode member are configured to be substantially flush, wherein the intravascular device has an electrical resistance of 100Ω or less between the electrode member and a second end portion that is opposite to the first end portion of the linear delivery member, and wherein the electrode member is electrically connected to the linear delivery member only at a distal tip on the first end portion side of the electrode member.

2. The intravascular device according to claim 1, wherein the first step-reducing portion and the second step-reducing portion comprise at least one of a coiled member provided around the linear delivery member, or a tubular member composed of resin and provided around the linear delivery member.

3. The intravascular device according to claim 2, wherein at least a portion of the coiled member extends within the electrode member.

4. The intravascular device according to claim 2, wherein at least a portion of the tubular member extends over the coiled member, the tubular member being the second step-reducing portion, and the coiled member being the first step-reducing portion.

5. The intravascular device according to claim 1, wherein the electrode member is in a form of a helically wound metal wire.

6. The intravascular device according to claim 1, wherein the electrode member and the linear delivery member are fused to each other.

7. The intravascular device according to claim 1, wherein the intravascular device is placed in a blood vessel for one day or more.

8. The intravascular device according to claim 1, wherein the blood vessel, in which the intravascular device is disposed, is a cerebral vein.

9. The intravascular device according to claim 1, wherein the linear delivery member has a smaller diameter portion provided on the first end portion side, has a larger diameter portion provided on a second end portion side, and has a conical surface portion provided between the smaller diameter portion and the larger diameter portion, the larger diameter portion being larger than the smaller diameter portion, and wherein the at least one electrode member is provided on the smaller diameter portion of the linear delivery member.

10. An intravascular device having a first end portion configured to be disposed within a blood vessel of a living organism, and comprising, on a first end portion side, an electrode that is configured to detect or stimulate activity in nerve tissue located outside of the blood vessel, the intravascular device further comprising:

a linear delivery member that is electrically conductive;

at least one electrode member provided on the first end portion side and electrically connected to the linear delivery member; and a step reducing portion that is configured to reduce a size of a step due to an outer diameter difference between an outer diameter of the electrode member and an outer diameter of the linear delivery member, wherein the linear delivery member has a smaller diameter portion provided on the first end portion side, has a larger diameter portion provided on a second end portion side, and has a conical surface portion provided between the smaller diameter portion and the larger diameter portion, the larger diameter portion being larger than the smaller diameter portion, wherein the outer diameter of the electrode member in a tip region of the electrode member, the tip region including a distal tip longitudinally aligned with the first end portion side, is configured such that a size of a step caused by an outer diameter difference between the outer diameter of the electrode member and the outer diameter of the linear delivery member reduces more than in a region other than the tip region of the electrode member, and wherein the intravascular device has an electrical resistance of 100Ω or less between the electrode member and a second end portion that is opposite to the first end portion of the linear delivery member.

11. The intravascular device according to claim 10, wherein the at least one electrode member is provided on the smaller diameter portion of the linear delivery member.

* * * * *